(12) United States Patent
Deshpande et al.

(10) Patent No.: US 12,246,274 B2
(45) Date of Patent: *Mar. 11, 2025

(54) SYSTEM AND METHOD FOR DISTILLATION

(71) Applicant: PRAJ INDUSTRIES LIMITED, Pune (IN)

(72) Inventors: Ghansham Baburao Deshpande, Pune (IN); Ajit Prabhakar Deshmukh, Pune (IN)

(73) Assignee: PRAJ INDUSTRIES LIMITED (IN)

( * ) Notice: Subject to any disclaimer, the term of this patent is extended or adjusted under 35 U.S.C. 154(b) by 0 days.

This patent is subject to a terminal disclaimer.

(21) Appl. No.: 18/672,158

(22) Filed: May 23, 2024

(65) Prior Publication Data

US 2024/0307795 A1 Sep. 19, 2024

Related U.S. Application Data

(63) Continuation of application No. 18/276,718, filed as application No. PCT/IN2023/050511 on Jun. 1, 2023.

(30) Foreign Application Priority Data

Jul. 1, 2022 (IN) .............................. 202221038264

(51) Int. Cl.
*B01D 3/00* (2006.01)
*B01D 1/00* (2006.01)
(Continued)

(52) U.S. Cl.
CPC ........... *B01D 3/148* (2013.01); *B01D 1/0058* (2013.01); *B01D 1/2881* (2013.01); *B01D 3/001* (2013.01);
(Continued)

(58) Field of Classification Search
CPC ...... B01D 3/001–005; C12H 6/02; C12F 3/10
See application file for complete search history.

(56) References Cited

U.S. PATENT DOCUMENTS

| 4,340,446 A | 7/1982 | Crawford |
| 8,114,255 B2 | 2/2012 | Vane et al. |

(Continued)

FOREIGN PATENT DOCUMENTS

| IN | 201921014261 A | 10/2020 |
| IN | 404737 | 8/2022 |

(Continued)

OTHER PUBLICATIONS

"Search Report and Written Opinion for PCT Application No. PCT/IN2023/050511 mailed Aug. 29, 2023".
"Indian Examination Report dated Mar. 18, 2024".

*Primary Examiner* — Jonathan Luke Pilcher
(74) *Attorney, Agent, or Firm* — Billion & Armitage

(57) ABSTRACT

The present invention relates to a system and method for distillation to reduce steam consumption has been disclosed. The system comprises of an analyser column 11, multiple pressure booster units (fan set-I 79, fan set-II 24, and fan set-III 29), a rectifier column 15, a plurality of evaporator units (30,12), a splitter unit 05, a plurality of de-superheating units (03, 80), and additional DDGS dryer unit 25. The integration of pressure booster units (fan set-I 79, fan set-II 24, and fan set-III 29) and additional DDGS dryer unit 05 increases the steam (vapor) production and reduces the steam (vapor) consumption in the system from external source and balances the optimization of process energy requirements, energy cost, and process carbon intensity.

19 Claims, 3 Drawing Sheets

(51) Int. Cl.
    *B01D 1/28*         (2006.01)
    *B01D 3/14*         (2006.01)
    *C12H 6/02*         (2019.01)

(52) U.S. Cl.
    CPC ............. *B01D 3/002* (2013.01); *B01D 3/005* (2013.01); *C12H 6/02* (2019.02)

(56) References Cited

U.S. PATENT DOCUMENTS

| | | |
|---|---|---|
| 8,182,654 B2 | 5/2012 | Sechrist et al. |
| 8,425,733 B2 | 4/2013 | Halvorsen et al. |
| 9,464,334 B2 | 10/2016 | Medoff et al. |
| 9,925,476 B2 | 3/2018 | Crawford et al. |
| 9,925,477 B2 | 3/2018 | Crawford et al. |
| 10,022,648 B2 | 7/2018 | Maedebach et al. |
| 10,267,511 B2 * | 4/2019 | Knight, Jr. ........... B01D 53/265 |
| 10,486,081 B2 | 11/2019 | Lee |
| 10,737,195 B2 * | 8/2020 | Brown ................ B01D 53/261 |
| 10,787,407 B2 | 9/2020 | Crawford et al. |
| 10,947,486 B1 | 3/2021 | Crawford et al. |
| 11,034,638 B2 | 6/2021 | Crawford et al. |
| 11,291,927 B2 | 4/2022 | Crawford et al. |
| 11,364,449 B2 | 6/2022 | Crawford et al. |
| 11,458,413 B2 | 10/2022 | Crawford et al. |
| 11,471,784 B2 | 10/2022 | Crawford et al. |
| 11,478,724 B2 | 10/2022 | Crawford et al. |
| 12,005,381 B2 * | 6/2024 | Zhou ...................... B01D 3/007 |
| 2018/0031227 A1 * | 2/2018 | Knight, Jr. .............. F26B 23/02 |
| 2018/0207543 A1 | 7/2018 | Lee |
| 2018/0290073 A1 * | 10/2018 | Brown ................... B01D 3/143 |
| 2023/0123549 A1 * | 4/2023 | Zhou ..................... B01D 3/001 |
| | | 203/71 |

FOREIGN PATENT DOCUMENTS

| | | |
|---|---|---|
| JP | 2011162502 A | 8/2011 |
| WO | 2014097311 A1 | 6/2014 |
| WO | 2016088134 A2 | 6/2016 |

* cited by examiner

SYSTEM AND METHOD FOR DISTILLATION

CROSS-REFERENCE TO RELATED APPLICATIONS AND PRIORITY

The present application claims priority from Indian patent application number (202221038264) filed on (Jan. 7, 2022), incorporated herein by a reference.

FIELD OF THE INVENTION

The present invention, in general, relates to an ethanol distillation system, and more particularly, relates to an improved ethanol distillation system having multiple sets of pressure booster units.

BACKGROUND OF THE INVENTION

Distillation or classical distillation enables the separation of two or more components or substances from a liquid mixture by using selective boiling and condensation temperatures. Further, the process may also be applied to separate two liquids having a different boiling point.

The distillation process may further be used for obtaining ethanol. The present ethanol distillation system use steam as an energy driver, wherein the steam is generated by burning natural gas/Coal/Fossil Fuel. However, the usage of such carbon-based fuel steam generation increases the greenhouse gas emission value, and the reduction of the energy requirement decreases the CI (Carbon Intensity) number for the production of ethanol.

Thus, there exists a long-felt need to design and develop an improved ethanol distillation system that does not rely on carbon-based fuel for steam generation.

SUMMARY OF THE INVENTION

Before the present disclosure for an improved system and method for ethanol distillation for reduction of steam is described, it is to be understood that this application is not limited to the particular systems, and methodologies described, as there can be multiple possible embodiments which are not expressly illustrated in the present disclosure. It is also to be understood that the terminology used in the description is for the purpose of describing the particular versions or embodiments only and is not intended to limit the scope of the present application. This summary is not intended to identify essential features of the claimed subject matter nor is it intended for use in determining or limiting the scope of the claimed subject matter.

In an implementation of the present disclosure, a method for distillation has been disclosed. The method may include transferring of a preheated feed stream to an analyser column for stripping vapor from the preheated feed stream. Further, compressing the stripped vapor in a fan set-I, in one or more stages to form compressed vapor. Further, transferring the compressed vapor from the fan set-I to a rectifier column and rectifying the compressed vapor in the rectifier column to obtain the rectified vapor. Further, transferring the rectified vapor from the rectifier column to an evaporator unit and condensing the rectified vapor to form rectified condensate in the evaporator unit. Further, transferring the rectified condensate to a dehydration section for further processing to obtain ethanol. The water vapor formed during the condensation process in the evaporator unit may be transferred to further fan set units.

In an implementation of the present disclosure, a system for distillation has been disclosed. The system as disclosed may comprise a preheater, an analyser column, a fan set-I, a rectifier column, and an evaporator unit. The analyser column may be configured to receive a preheated feed stream from the preheater, and may be configured to strip-off the vapor from the received preheated feed stream. Further the fan set-I may be configured to receive the stripped vapor from the analyser column and may be configured to compress the stripped vapor in one or more stages to form a compressed vapor. Further, the rectifier column may be configured to receive the compressed vapor from the fan set-I and may be configured to rectify the compressed vapor to form a rectified vapor. The evaporator unit may be configured to receive the rectified vapor from the rectifier column and may be configured to condense the rectified vapor to form a rectified condensate. Further, the evaporator unit may be configured to transfer the rectified condensate to a dehydration section for further concentration of ethanol from the rectified condensate. The water vapor formed during the condensation process in the evaporator unit may be transferred to further fan set units.

BRIEF DESCRIPTION OF DRAWINGS

The detailed description is described with reference to the accompanying figures. The same numbers are used throughout the drawings to refer like features and components.

DETAILED DESCRIPTION OF THE INVENTION

Figure 1:
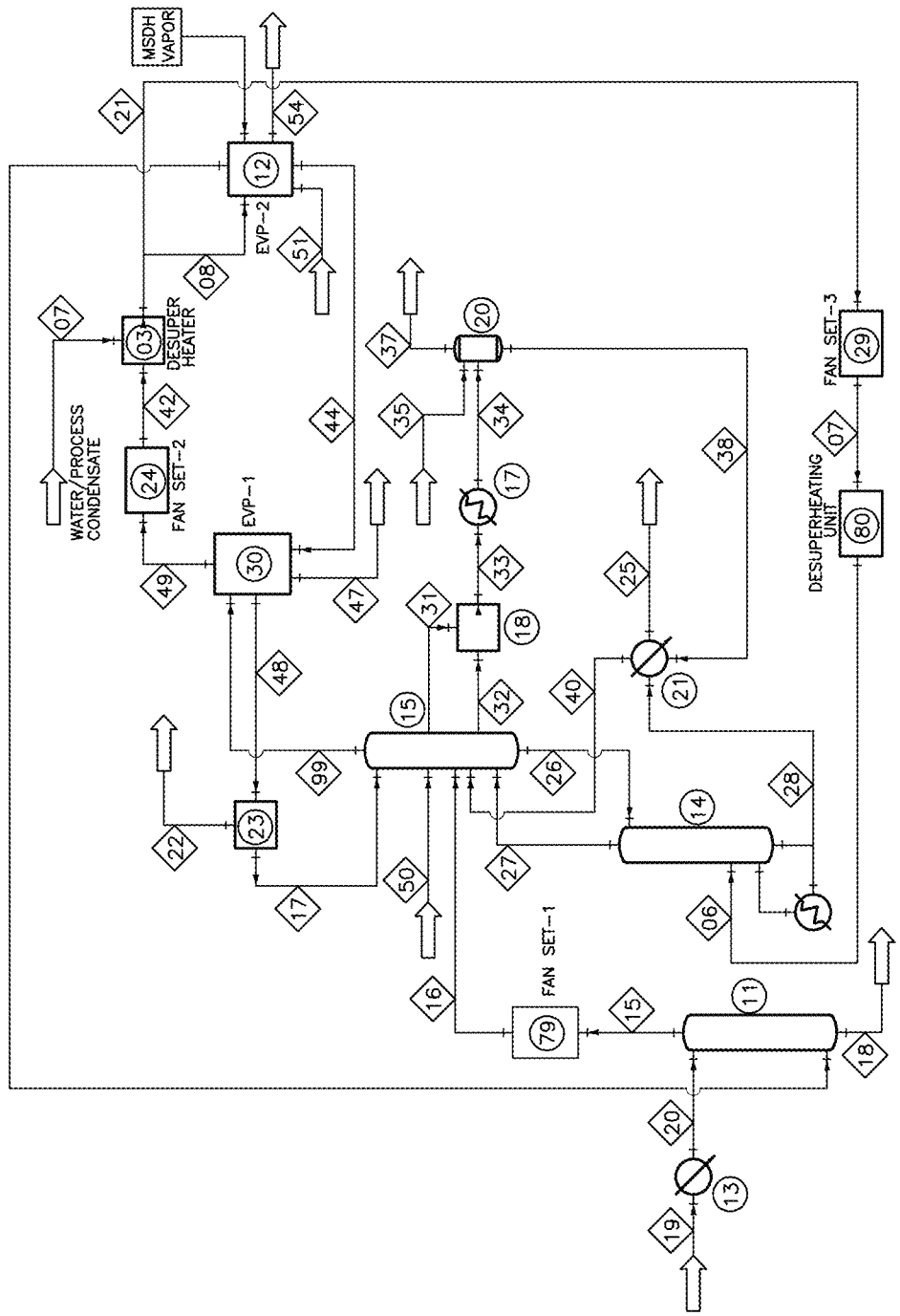
FIG. 1. illustrates a system and method for distillation, in accordance with an exemplary embodiment.

Reference throughout the specification to "various embodiments," "some embodiments," "one embodiment," or "an embodiment" means that a particular feature, structure, or characteristic described in connection with the embodiment is included in at least one embodiment. Thus, appearances of the phrases "in various embodiments," "in some embodiments," "in one embodiment," or "in an embodiment" in places throughout the specification are not necessarily all referring to the same embodiment. Furthermore, the particular features, structures or characteristics may be combined in any suitable manner in one or more embodiments. Following is an example which is illustrative only and invention accommodates any and every variation of the example provided below that shall serve the same purpose and is obvious to a person skilled in the art.

The present subject matter relates to a system and method for distillation for reduced steam consumption. The system comprises a preheater, an analyser column, a rectifier column, a first and second evaporator units, a first and second de-superheating units, multiple pressure booster units (Fan Set I, II, and III) and an exhaust column. The Fan Set units may comprise a multiple set of fans. The Fan Set units may be placed at multiple locations for pressurizing the vapors and substituting it with fuel-based steam during the distillation cycle. Further, the method may include preheating a fermented wash in the preheater and feeding a preheated feed stream to the analyser column. The analyser column may perform stripping of vapor from the preheated feed stream. Further, the stripped vapor may be fed to the Fan set I. The Fan set I may be configured to pressurise the stripped vapor to obtain compressed vapor in one or more stages. Further, the compressed vapor may be fed to the rectifier column. The compressed vapor may increase the operating pressure and temperature of the rectifier column, and thereby increases throughput of the rectifier column. Also, rectifier may be configured to receive feed from a dehydration section for recovery of ethanol. The rectifier column may be configured to rectify the compressed vapor to obtain rectified vapor. Further, the rectified vapor from rectifier column may be fed to the first evaporator unit for condensation. The first evaporator unit may be configured to fed part of condense vapor to the rectifier as reflux and left over condense vapor to the dehydration section for further concentration of ethanol.

Further, the water vapor from the first evaporator may be fed to the Fan set II. The Fan set II may be configured to pressurise the water vapor to superheated water vapor in one or more stages. The superheated water vapor may be fed to the first de-superheater unit to obtain saturated water vapor. Further the saturated water vapor may be fed to the splitter unit. The splitter unit may be configured to split the saturated water vapor into first and second saturated water vapor streams. Further, the second saturated water vapor stream may be fed to the second evaporator unit. The second evaporator unit may also receive additional saturated water vapor stream from the dehydration section along with second saturated water vapor stream from the splitter unit. Further, the second saturated water vapor stream and additional saturated water vapor stream may be fed to the analyser column to act as a heat source. Further, the first saturated water vapor stream from the splitter unit may be received by the Fan set III. The fan set III may be configured to compress the first saturated water vapor stream in one or more stages to obtain superheated water vapor. Further, the second de-superheater unit may be configured to receive and de-superheat the superheated water vapor to obtain saturated water vapor. The saturated water vapor may be further received by the exhaust column to act as a heat source.

Referring to FIG. 1 illustrates a system and method for distillation for reduction of Steam, in accordance with an exemplary embodiment. The system 100 may comprise a preheater 13. The preheater may further be connected to an analyser column 11. The analyser column 11 may be further connected to a first pressure booster (Fan Set I unit), wherein the Fan Set I unit may comprise a first set of fans 79. The first set of fans 79 may be configured to increase pressure in one or more stages in series. Further, the first set of fans 79 may be connected to a rectifier column 15. Further, the rectifier column 15 may be connected to a first evaporator unit 30. Further, the first evaporator unit 30 may be connected to a second pressure booster unit (Fan Set II unit), the Fan Set II unit may comprise a second set of fans 24. The second set of fans 24 may be configured to increase pressure in one or more stages in series. The second set of fans 24 may be further connected to a first de-superheating unit 03. Further, the first de-superheating unit 03 may be connected to a splitter unit 05, the splitter unit may be further connected to a second evaporator unit 12 and a third pressure booster (Fan Set III unit), the Fan Set III unit may comprise a third set of fans 29. The second evaporator unit 12 may be further connected to the analyser column 11 and the third set of fans 29 may be connected to a second de-superheating unit 80. Further, the second de-superheating unit 80 may be connected to an exhaust column 14.

Further, in accordance with the exemplary embodiment, a fermented wash 19 containing 8-20% v/v ethanol concentration may be preheated at 60-70 degree temperature in the feed preheater 13 to obtain a preheated feed stream 20. The preheated feed stream 20 may be fed to the analyser column 11 for stripping of ethanol and water stream of the preheated feed stream 20 to obtain stripped vapor 15' from the top of the analyser column 11 operating at a pressure of 0.4 to 0.6 bar and at a temperature of 72-75 degree Centigrade. The stripped vapor 15' at top of the analyser column 11 may contain 45-65% v/v of ethanol and 30-55% of water. Further, the stripped vapor 15' may be compressed by the Fan Set-I 79 in one or more stages to obtain compressed vapor 16 at a pressure of 1.2-1.3 bar. The obtained compressed vapor 16 may comprise ethanol and water stream at pressure 1.2-1.3 bar and flow rate of 33305 kg/h.

Further, the compressed vapor 16 at a pressure of 1.2-1.3 bar, at a temperature of 140-160 degree, and at a flow rate of 33305 kg/h may be transferred to the rectifier column 15 by the fan set-I 79 for the further rectification process. The transfer of high pressure and high temperature compressed vapor 16 to the rectifier column 15 may increase operating pressure and of rectifier column 15 and thereby may result in higher throughput to obtain rectified vapor 99. The rectified vapor 99 having temperature between 80-90 degree, pressure between 1.10-1.20 bar, and flowrate of 71710 kg/h present at the top of the rectifier column 15 may be further transferred to the first evaporator unit 30 for condensation process. The rectified vapor 99 may be condensed to form rectified condensate 48 in the first evaporator unit 30.

The part of rectified condensate 48 from the first evaporator unit 30 may be transferred back to the rectifier column 15 as a reflux 17 and the remaining rectified condensate 48 may be transferred to dehydration section 89 for further concentration of ethanol from the rectified condensate 48. After condensation process the first evaporator unit 30 may comprise of water vapor 49 at temperature between 65-75-degree, pressure 0.2-0.4 Bar, and flowrate of 27520 kg/h. The water vapors 49 present at the top of the first evaporator unit 30 may be transferred to the Fan Set-II 24. The Fan Set-II 24 may be configured to compress the water vapor 49 from 0.3 bar to 0.9 bar to obtain superheated water vapor 42 in one or more stages.

The superheated water vapors 42 may be received by the first de-superheating unit 03. The first de-superheating unit 03 may be configured to de-superheat the superheated water vapor 42 to obtain saturated water vapor 53. Further, the saturated water vapor 53 may be received by the splitter unit 05. The splitter unit 05 may be configured to split the saturated water vapor 53 into saturated first water vapor stream 21 and saturated second water vapor stream 08. Further the saturated second water vapor stream 08 at the pressure between 0.8-0.10 bar, temperature 96-99 degree, and flow rate of 20100 kg/h may be transferred to the second evaporator unit 12 by the splitter unit 05. Further, the second evaporator unit 12 may be configured to receive an additional saturated water vapor stream 90 from the dehydration section 89. The additionally received saturated water vapor stream 90 from the dehydration section 89 and saturated second water vapor stream 08 received from the splitter unit 05 may combine to form combined saturated water vapor 43. The second evaporator unit 12 may be configured to transfer the combined saturated water vapor 43 at a pressure of 0.4-0.6 bar, temperature of 80-90 degree, and flow rate of 24300 kg/h back to the analyser column 11 to make combined saturated water vapor 43 may act as a heat source.

Further the splitter unit 05 may be configured to transfer the saturated first water vapor stream 21 at a pressure of 0.8-0.10 bar and flow rate of 9800 kg/h to the fan set-III 29. The fan set-III 29 may be configured to compress the saturated first water vapor stream 21 to a pressure of 2.1 bar to form superheated water vapor 07 at flow rate of 9821 kg/h. Further, the superheated water vapor 07 may be transferred to second de-superheating unit 80. The second de-superheating unit 80 may be configured to de-superheat the superheated water vapor 07 to obtain saturated water vapor 06 at pressure of 2.1 bar, temperature of 127° C. and flowrate of 10471 kg/h. The saturated water vapor 06 at flow rate of 6800 kg/h may be received by the exhaust column 14 to make saturated water vapor 06 may act as a heat source.

Figure 2:
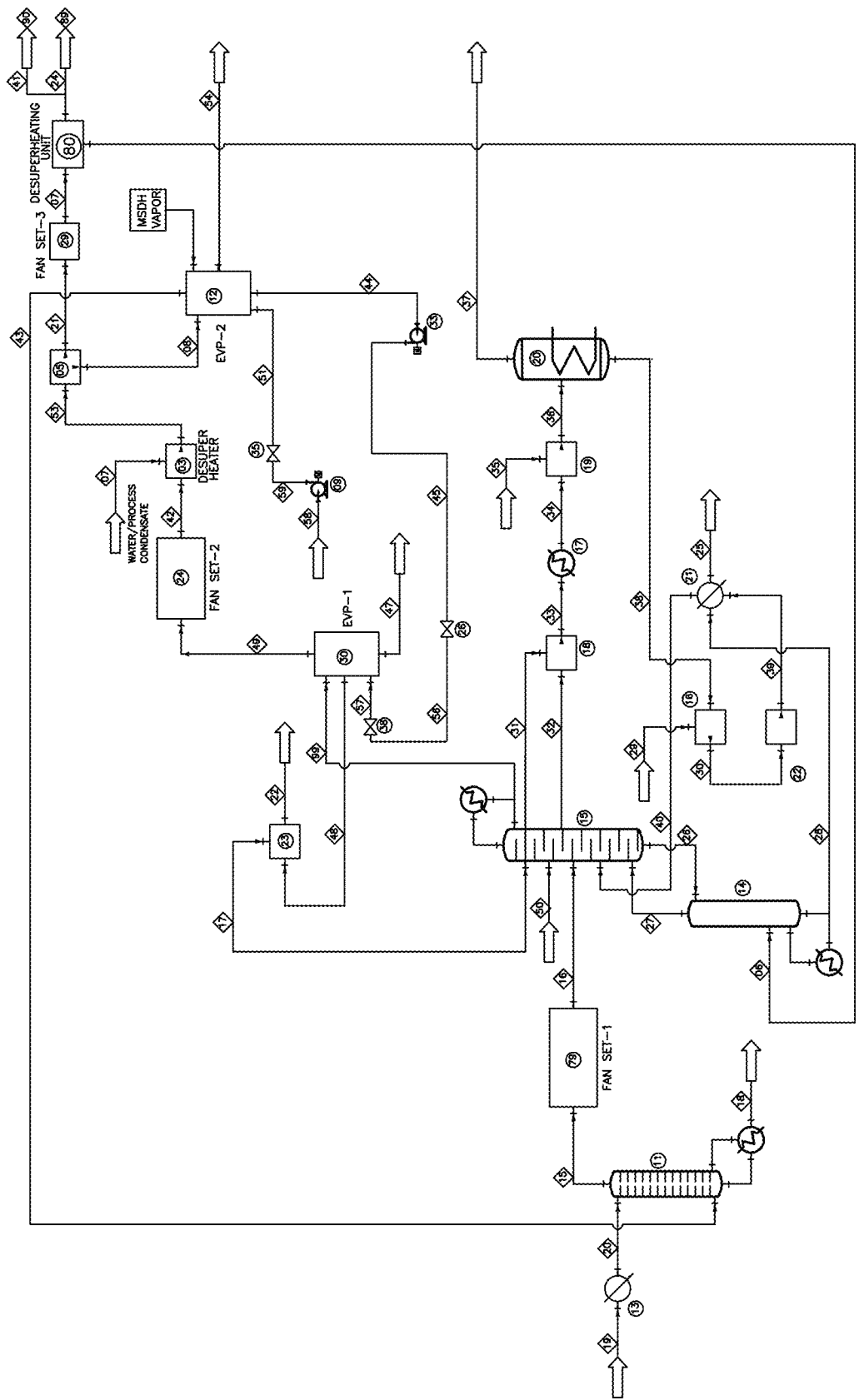
FIG. 2. illustrates a liquefication and a dehydration section associated with a system and method for distillation, in accordance with an exemplary embodiment.

Referring to FIG. 2 illustrates a system and method for distillation for reduction of steam, in accordance with an exemplary embodiment. The system 100 may comprise a preheater 13. The preheater may further be connected to an analyser column 11. The analyser column 11 may be further connected to a first pressure booster (Fan Set I unit), wherein the Fan Set I unit may comprise a first set of fans 79. The first set of fans 79 may be configured to increase pressure in one or more stages in series. Further, the first set of fans 79 may be connected to a rectifier column 15. Further, the rectifier column 15 may be connected to a first evaporator unit 30. Further, the first evaporator unit 30 may be connected to a second pressure booster unit (Fan Set II unit), the Fan Set II unit may comprise a second set of fans 24. The second set of fans 24 may be configured to increase pressure in one or more stages in series. The second set of fans 24 may be further connected to a first de-superheating unit 03. Further, the first de-superheating unit 03 may be connected to a splitter unit 05, the splitter unit may be further connected to a second evaporator unit 12 and a third pressure booster (Fan Set III unit), the Fan Set III unit may comprise a third set of fans 29. The second evaporator unit 12 may be further connected to the analyser column 11 and the third set of fans 29 may be connected to a second de-superheating unit 80. Further, the second de-superheating unit 80 may be connected to an exhaust column 14, a liquefaction section 90, and a dehydration section 89.

Further, in accordance with the exemplary embodiment, a fermented wash 19 containing 8-20% v/v ethanol concentration may be preheated at 60-70 degree temperature in the feed preheater 13 to obtain a preheated feed stream 20. The preheated feed stream 20 may be fed to the analyser column 11 for stripping of ethanol and water stream of the preheated feed stream 20 to obtain stripped vapor 15' from the top of the analyser column 11 operating at a pressure of 0.4 to 0.6 bar and at a temperature of 72-75 degree Centigrade. The stripped vapor 15' at top of the analyser column 11 may contain 45-65% v/v of ethanol and 30-55% of water. Further, the stripped vapor 15' may be compressed by the Fan Set-I 79 in one or more stages to obtain compressed vapor 16 at a pressure of 1.2-1.3 bar. The obtained compressed vapor 16 may comprise ethanol and water stream at pressure 1.2-1.3 bar and flow rate of 33305 kg/h.

Further, the compressed vapor 16 at a pressure of 1.2-1.3 bar, at a temperature of 140-160 degree, and at a flow rate of 33305 kg/h may be transferred to the rectifier column 15 by the fan set-I 79 for the further rectification process. The transfer of high pressure and high temperature compressed vapor 16 to the rectifier column 15 may increase operating pressure and of rectifier column 15 and thereby may result in higher throughput to obtain rectified vapor 99. The rectified vapor 99 having temperature between 80-90 degree, pressure between 1.10-1.20 bar, and flowrate of 71710 kg/h present at the top of the rectifier column 15 may be further transferred to the first evaporator unit 30 for condensation process. The rectified vapor 99 may be condensed to form rectified condensate 48 in the first evaporator unit 30.

The part of rectified condensate 48 from the first evaporator unit 30 may be transferred back to the rectifier column 15 as a reflux 17 and the remaining rectified condensate 48 may be transferred to the dehydration section 89 for further concentration of ethanol from the rectified condensate 48. After condensation process the first evaporator unit 30 may comprise of water vapor 49 at temperature between 65-75-degree, pressure 0.2-0.4 Bar, and flowrate of 27520 kg/h. The water vapors 49 present at the top of the first evaporator unit 30 may be transferred to the Fan Set-II 24. The Fan Set-II 24 may be configured to compress the water vapor 49 from 0.3 bar to 0.9 bar to obtain superheated water vapor 42 in one or more stages.

The superheated water vapor 42 may be received by the first de-superheating unit 03. The first de-superheating unit 03 may be configured to de-superheat the superheated water vapor 42 to obtain saturated water vapor 53. Further, the saturated water vapor 53 may be received by the splitter unit 05. The splitter unit 05 may be configured to split the saturated water vapor 53 into saturated first water vapor stream 21 and saturated second water vapor stream 08. Further the saturated second water vapor stream 08 at the pressure between 0.8-0.10 bar, temperature 96-99 degree, and flow rate of 20100 kg/h may be transferred to the second evaporator unit 12 by the splitter unit 05. Further, the second evaporator unit 12 may be configured to receive an additional saturated water vapor stream 90 from the dehydration section 89. The additionally received saturated water vapor stream 90 from the dehydration section 89 and saturated second water vapor stream 08 received from splitter unit 05 may combine to form combined saturated water vapor 43. The second evaporator unit 12 may be configured to transfer the combined saturated water vapor 43 at a pressure of 0.4-0.6 bar, temperature of 80-90 degree, and flow rate of 24300 kg/h back to the analyser column 11 to make combined saturated water vapor 43 may act as a heat source.

Further the splitter unit 05 may be configured to transfer the saturated first water vapor stream 21 at a pressure of 0.8-0.10 bar and flow rate of 9800 kg/h to the fan set-III 29. The fan set-III 29 may be configured to compress the saturated first water vapor stream 21 to a pressure of 2.1 bar to form superheated water vapor 07 at flow rate of 9821 kg/h. Further, the superheated water vapor 07 may be transferred to second de-superheating unit 80. The second de-superheating unit 80 may be configured to de-superheat the superheated water vapor 07 to obtain saturated water vapor 06 at pressure of 2.1 bar, temperature of 127° C. and flowrate of 10471 kg/h, a saturated water vapor 41 for the liquefaction section 90 at flowrate of 3671 kg/h, and a saturated water vapor 24 for the dehydration section 89. The saturated water vapor 06 at flow rate of 6800 kg/h may be received by the exhaust column 14, the saturated water vapor 41 may be received by the liquefaction section 90, and the saturated water vapor 24 may be received by the dehydration section 89 to act as a heat source.

Figure 3:
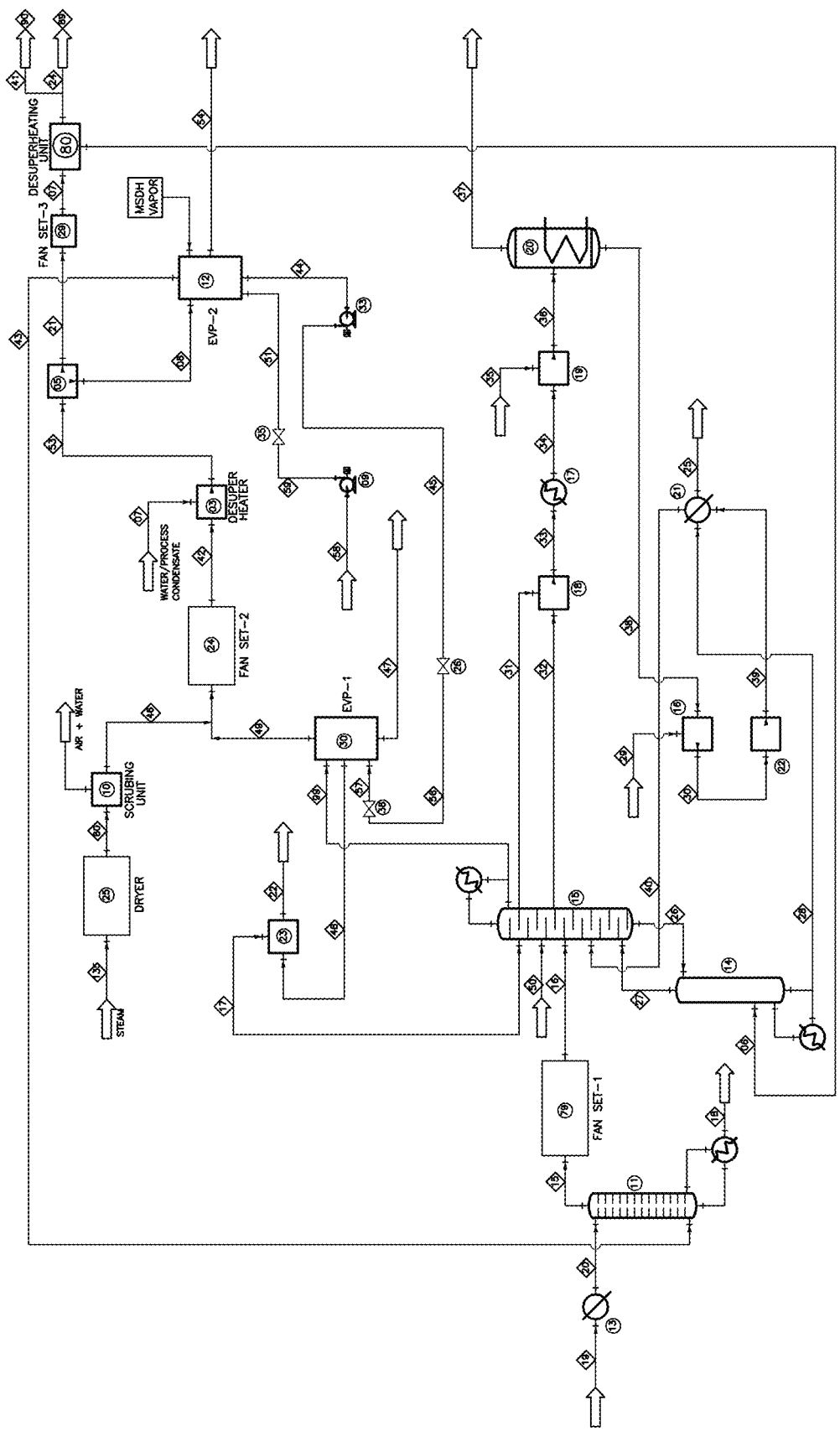
FIG. 3. illustrates a DDGS dryer system associated with a system and method for distillation, in accordance with an exemplary embodiment.

Referring to FIG. 3 illustrates a DDGS dryer system associated with the system and method for distillation for reduction of steam, in accordance with an exemplary embodiment. The system 100 may comprise a preheater 13. The preheater may further be connected to an analyser column 11.

The analyser column 11 may be further connected to a first pressure booster (Fan Set I unit), the Fan Set I unit may comprise a first set of fans 79. The first set of fans 79 may be configured to increase pressure in one or more stages in series. Further, the first set of fans 79 may be connected to a rectifier column 15. Further, the rectifier column 15 may be connected to a first evaporator unit 30. The first evaporator unit 30 may be connected to a second pressure booster unit (Fan Set II unit), the Fan Set II unit may comprise a second set of fans 24. The second set of fans 24 may be configured to increase pressure in one or more stages in series. Further an additional DDGS dryer unit 25 may also be connected to the second set of fans 24 through a scrubbing unit 10. The second set of fans 24 may be further connected to a first de-superheating unit 03. Further, the first de-superheating unit 03 may be connected to a splitter unit 05, the splitter unit may be further connected to a second evaporator unit 12 and a third pressure booster (Fan Set III unit), the Fan Set III unit may comprise a third set of fans 29. The second evaporator unit 12 may be further connected to the analyser column 11 and the third set of fans 29 may be connected to a second de-superheating unit 80. Further, the second de-superheating unit 80 may be connected to an exhaust column 14, a liquefaction section 90, and a dehydration section 89.

Further, in accordance with the exemplary embodiment, a fermented wash 19 containing 8-20% v/v ethanol concentration may be preheated at 60-70 degree temperature in the feed preheater 13 to obtain a preheated feed stream 20. The preheated feed stream 20 may be fed to the analyser column 11 for stripping of ethanol and water stream of the preheated feed stream 20 to obtain stripped vapor 15' from the top of the analyser column 11 operating at a pressure of 0.4 to 0.6 bar and at a temperature of 72-75 degree Centigrade. The stripped vapor 15' at top of the analyser column 11 may contain 45-65% v/v of ethanol and 30-55% of water. Further, the stripped vapor 15' may be compressed by the Fan Set-I 79 in one or more stages to obtain compressed vapor 16 at a pressure of 1.2-1.3 bar. The obtained compressed vapor 16 may comprise ethanol and water stream at pressure 1.2-1.3 bar and flow rate of 33305 kg/h.

Further, the compressed vapor 16 at a pressure of 1.2-1.3 bar, at a temperature of 140-160 degree, and at a flow rate of 33305 kg/h may be transferred to the rectifier column 15 by the fan set-I 79 for the further rectification process. The transfer of high pressure and high temperature compressed vapor 16 to the rectifier column 15 may increase operating pressure and of rectifier column 15 and thereby may result in higher throughput to obtain rectified vapor 99. The rectified vapor 99 having temperature between 80-90 degree, pressure between 1.10-1.20 bar, and flowrate of 71710 kg/h present at the top of the rectifier column 15 may be further transferred to the first evaporator unit 30 for condensation process. The rectified vapor 99 may be condensed to form rectified condensate 48 in the first evaporator unit 30.

The part of rectified condensate 48 from the first evaporator unit 30 may be transferred back to the rectifier column 15 as a reflux 17 and the remaining rectified condensate 48 may be transferred to the dehydration section 89 for further concentration of ethanol from the rectified condensate 48. After condensation process the first evaporator unit 30 may comprise of water vapor 49 at temperature between 65-75-degree, pressure 0.2-0.4 Bar, and flowrate of 27520 kg/h. The water vapor 49 present at the top of the first evaporator unit 30 may be transferred to the Fan Set-II 24. Further the DDGS dryer unit 25 may transfer a dryer water vapor 60 to the scrubbing unit 10. The scrubbing unit 10 may be configured to purify the dryer water vapor 60 to obtain purified water vapor 46. The Fan Set-II 24 may be configured to receive the water vapor 49 from the first evaporator unit 30 and purified water vapor 46 from the scrubbing unit 10. The water vapor 49 may be at 0.2-0.4 bar pressure, flow rate of 27520 kg/h, and temperature of 65-75 degree and purified water vapor 46 may be at 0.2-0.4 bar pressure, flow rate of 13750 kg/h, and temperature of 70-80 degree may get compressed by the Fan Set-II 24 in one or more stages to obtain superheated water vapor 42 at pressure 0.7-0.9 bar and flow rate of 41270 kg/h.

The superheated water vapor 42 may be received by the first de-superheating unit 03. The first de-superheating unit 03 may be configured to de-superheat the superheated water vapor 42 to obtain saturated water vapor 53. Further, the saturated water vapor 53 may be received by the splitter unit 05. The splitter unit 05 may be configured to split the saturated water vapor 53 into saturated first water vapor stream 21 and saturated second water vapor stream 08. Further the saturated second water vapor stream 08 at the pressure between 0.7-0.9 bar, temperature 120-130 degree, and flow rate of 20100 kg/h may be transferred to the second evaporator unit 12 by the splitter unit 05. Further, the second evaporator unit 12 may be configured to receive an additional saturated water vapor stream 90 from the dehydration section 89. The additionally received saturated water vapor stream 90 from the dehydration section 89 and saturated second water vapor stream 08 received from splitter unit 05 may combine to form combined saturated water vapor 43. The second evaporator unit 12 may be configured to transfer the combined saturated water vapor 43 at a pressure of 0.4-0.6 bar, temperature of 80-90 degree, and flow rate of 24300 kg/h back to the analyser column 11 to make combined saturated water vapor 43 may act as a heat source.

Further the splitter unit 05 may be configured to transfer the saturated first water vapor stream 21 at a pressure of 0.7-0.9 bar, temperature of 90-100 degree, and flow rate of 24716 kg/h to the fan set-III 29. The fan set-III 29 may be configured to compress the saturated first water vapor stream 21 to a pressure of 2.1 bar to form superheated water vapor 07 at flow rate of 26516 kg/h. Further, the superheated water vapor 07 may be transferred to second de-superheating unit 80. The second de-superheating unit 80 may be configured to de-superheat the superheated water vapor 07 to obtain saturated water vapor 06 at pressure of 2.1 bar, temperature of 127° C. and flowrate of 26516 kg/h, a saturated water vapor 41 for the liquefaction section 90 at flowrate of 3671 kg/h, and a saturated water vapor 24 for the dehydration section 89. The saturated water vapor 06 at flow rate of 6800 kg/h may be received by the exhaust column 14, the saturated water vapor 41 may be received by the liquefaction section 90, and the saturated water vapor 24 may be received by the dehydration section 89 to act as a heat source.

The implementation of the above schematics may reduce steam consumption in the liquefication and dehydration section (not shown in the figure) due to additional water vapor fed from Fan Set III. Wherein, the additional water vapor may be generated by the association of DDGS Dryer with the current system. Further reduction of steam consumption in the liquefication and dehydration section may be configured to balance the optimization of process energy requirements, energy cost, and process carbon intensity.

The foregoing description shall be interpreted as illustrative and not in any limiting sense. A person of ordinary skill in the art would understand that certain modifications could come within the scope of this disclosure. The embodiments, examples and alternatives of the preceding paragraphs or the description and drawings, including any of their various aspects or respective individual features, may be taken independently or in any combination. Features described in connection with one embodiment are applicable to all embodiments unless such features are incompatible.

The improved system and method for ethanol distillation of the present subject matter has, but is not limited to, the following benefits/advantages:

No steam required.

useful for ethanol concentration and moisture removal.

pressure booster units compress intermediate stream (Mash Column top vapors) instead of using biofuel steam.

Increased pressure of rectifier column leads to additional distillation capacity and leading to modernization of ethanol plant capacity.

reduction of steam consumption in the liquefication and dehydration section due to additional water vapors generated in the Fan Set II unit and Fan Set III unit reduces the dependency of the system on additional fuel-generated steam from outside sources.

optimizes process energy requirements, energy cost, and process carbon intensity

LIST OF REFERENCE NUMERALS

19 Fermented wash
13 Preheater
20 Preheated feed stream
15' Stripped vapor
79 Fan set-I
16 Compressed vapor
15 Rectifier column
99 Rectified vapor
30 First evaporating unit
17 Reflux
49 Water vapor
25 DDGS dryer unit
60 Dryer water vapor
10 Scrubbing unit
46 Purified water vapor
24 Fan set-II
42 Superheated water vapor
03 First de-superheating unit
53 Saturated water vapor
05 Splitter unit
21 First water vapor stream
08 Second water vapor stream
12 Second evaporating unit
43 Combined saturated water vapor
29 Fan set-III
07 Superheated water vapor
80 Second de-superheating unit
06 Saturated water vapor
14 Exhaust column
41 saturated water vapor for the liquefaction section
90 Liquefaction section
24 saturated water vapor for the dehydration section
89 Dehydration section

We claim:

1. A system for ethanol separation, the system comprising:
an analyzer unit configured to produce a stripped vapor stream from a feed stream, wherein the stripped vapor stream includes ethanol and water;
one or more first compressors configured to compress the stripped vapor stream to produce a first compressed vapor stream;
a rectifier unit configured to receive the first compressed vapor stream and to produce a rectified vapor stream;
a first evaporator configured to receive the rectified vapor stream and to form an evaporator vapor stream and a condensate stream; and
one or more second compressors configured to compress the evaporator vapor stream to form a second compressed stream.

2. The system of claim 1 further comprising a preheater configured to heat the feed stream, wherein the feed stream includes fermented wash.

3. The system of claim 1, wherein the one or more first compressors and the one or more second compressors each include two or more compressor stages.

4. The system of claim 1, wherein the condensate stream is transferred to at least one of the rectifier unit and a dehydration system.

5. The system of claim 1 further comprising a second evaporator downstream from the one or more second compressors, wherein the second evaporator is in fluid communication with the analyzer unit.

6. The system of claim 1 further comprising one or more third compressors downstream from the one or more second compressors.

7. The system of claim 6 further comprising an exhaust column in fluidic communication with the rectifier unit.

8. The system of claim 7, wherein the exhaust column is configured to receive vapor that has been compressed by the one or more third compressors.

9. The system of claim 6, wherein the one or more third compressors is in fluid communication with a dehydration system.

10. The system of claim 1 further comprising a dryer configured to form a dryer vapor stream.

11. The system of claim 10 further comprising a scrubbing unit downstream from the dryer, wherein the scrubbing unit includes a scrubber and is configured to receive the dryer vapor stream and configured to form a purified vapor stream.

12. The system of claim 11, wherein the scrubbing unit is in fluid communication with the one or more second compressors, and wherein the one or more second compressors is configured to receive the evaporator vapor stream and the purified vapor stream.

13. A system for ethanol separation, the system comprising:
an analyzer unit configured to produce a stripped vapor stream from a feed stream, wherein the stripped vapor stream includes ethanol and water;
one or more first compressors configured to compress the stripped vapor stream to produce a first compressed vapor stream;
a rectifier unit configured to receive the first compressed vapor stream and to produce a rectified vapor stream; and
a first evaporator configured to receive the rectified vapor stream and to form an evaporator vapor stream and a condensate stream,
wherein the evaporator vapor stream is utilized in one or more downstream processing units to form saturated water vapor, wherein the saturated water vapor is utilized as a heat source for one or more of a second evaporator, the analyzer unit, an exhaust column in fluid communication with the rectifier unit, and a dehydration system,
wherein the condensate stream is transferred to at least one of the rectifier unit and a dehydration system.

14. The system of claim 13, further comprising a preheater configured to heat the feed stream, wherein the feed stream includes fermented wash.

15. The system of claim 13, wherein the one or more downstream processing units includes one or more second compressors and one or more third compressors downstream from the one or more second compressors.

16. A method of ethanol purification, the method comprising:
   processing a feed stream including fermented wash to form a stripped vapor stream, wherein the stripped vapor stream includes ethanol and water;
   compressing the stripped vapor stream to produce a first compressed vapor stream;
   processing the first compressed vapor stream in a rectifier unit to form a rectified vapor stream;
   processing the rectified vapor stream to form an evaporator vapor stream and a condensate stream; and
   compressing the evaporator vapor stream and a purified vapor stream from a scrubbing unit to form a second compressed stream, wherein the scrubbing unit includes a scrubber.

17. The method of claim 16 further comprising heating the feed stream prior to processing the feed stream, and transferring the condensate stream to at least one of the rectifier unit and a dehydration system.

18. The method of claim 16 further comprising desuperheating the second compressed stream to form a saturated vapor stream including water.

19. The method of claim 18 further comprising compressing the saturated vapor stream for transferring energy to at least one of an exhaust column and a dehydration system.

* * * * *